United States Patent [19]

Paget

[11] 4,064,261

[45] Dec. 20, 1977

[54] AGENT FOR THE CONTROL OF PLANT-PATHOGENIC ORGANISMS

[75] Inventor: Charles J. Paget, Indianapolis, Ind.

[73] Assignee: Eli Lilly and Company, Indianapolis, Ind.

[21] Appl. No.: 556,767

[22] Filed: Mar. 10, 1975

Related U.S. Application Data

[63] Continuation of Ser. No. 296,380, Oct. 10, 1972, abandoned, which is a continuation-in-part of Ser. No. 243,838, April 13, 1972, abandoned, which is a continuation-in-part of Ser. No. 188,546, Oct. 12, 1971, abandoned.

[51] Int. Cl.² ............... A01N 9/12; A01N 9/22; C07D 277/82
[52] U.S. Cl. ............... 424/270; 424/269; 424/272; 260/305; 260/301; 260/307 D
[58] Field of Search ............ 260/305, 307 D, 302 H; 424/269, 270, 272

[56] References Cited

U.S. PATENT DOCUMENTS

| 2,786,054 | 3/1957 | Brooker et al. | 260/240.6 |
| 2,852,384 | 9/1958 | Brooker et al. | 96/102 |
| 2,861,076 | 11/1958 | Knott et al. | 260/305 |
| 2,870,014 | 1/1959 | Brooker et al. | 96/106 |
| 2,891,862 | 6/1959 | Van Allan | 96/67 |

OTHER PUBLICATIONS

Sycheva et al., "Khim Geterotsikl Soedin," 1970, (7), pp. 916–919.

*Primary Examiner*—V. D. Turner
*Attorney, Agent, or Firm*—Kathleen R. S. Page; Everet F. Smith

[57] ABSTRACT

Methods employing and compositions comprising, for the control of plant-pathogenic organisms, specified triazolobenzoxazole and triazolobenzothiazole compounds; and novel methods for the preparation of the compounds.

18 Claims, No Drawings

AGENT FOR THE CONTROL OF PLANT-PATHOGENIC ORGANISMS

CROSS-REFERENCES TO RELATED APPLICATIONS

This is a continuation of my copending application Ser. No. 296,380, filed Oct. 10, 1972 and abandoned after the filing of this application. Application Ser. No. 296,380 was, in turn, a continuation-in-part of my then copending application Ser. No. 243,838, filed Apr. 13, 1972, and abandoned after the filing of application Ser. No. 296,380. Application Ser. No. 243,838 was, in turn, a continuation-in-part of my then copending application Ser. No. 188,546, filed Oct. 12, 1971, and abandoned after the filing of application Ser. No. 243,838.

SUMMARY OF THE INVENTION

The present invention is directed to novel methods employing and compositions comprising, for the control of plant-pathogenic organisms, triazolobenzoxazole and triazolobenzothiazole compounds of the formula:

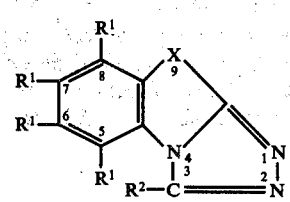
I.

and the phytologically acceptable acid addition salts thereof. In the above and succeeding formulae, X represents —O—, —S—,

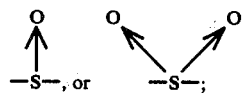

each $R^1$ independently represents hydrogen, halo, lower alkyl of $C_1$–$C_3$, lower alkoxy of $C_1$–$C_3$, or lower alkylthio of $C_1$–$C_3$;

$R^2$ represents hydrogen, alkyl of $C_1$–$C_{11}$, cyclopropyl, hydroxy, lower alkoxy of $C_1$–$C_3$, mercapto, lower alkylthio of $C_1$–$C_3$, allylthio, propynylthio, benzylthio, halo, amino, (lower alkyl of $C_1$–$C_3$)amino, di(lower alkyl of $C_1$–$C_3$)amino, carbamoyl, thiocyanato, acetamido, trifluoromethyl, radical of the formula

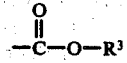

wherein $R^3$ represents sodium, potassium, or lower alkyl of $C_1$–$C_3$, halomethyl, or mono- or di(lower alkyl of $C_1$–$C_3$)aminomethyl;

subject to the limitations (1) that at least two $R^1$'s, or at least one $R^1$ and $R^2$, represent hydrogen; and (2) that when both $R^2$ and the $R^1$ substituent at the 5-position represent groups other than hydrogen, such groups together do not contain more than six carbon atoms.

The compounds defined above are useful for the control of plant-pathogenic organisms. Thus the present invention is directed to methods employing and compositions comprising these compounds for the control of such organisms. Certain of these compounds exhibit a high degree of systemic activity and are claimed as new compounds. These compounds are 3-chloro-s-triazolo(3,4-b)benzothiazole; 5-chloro-s-triazolo(3,4-b)benzothiazole; 5-fluoro-s-triazolo(3,4-b)benzothiazole; and 5-methyl-s-triazolo(3,4-b)benzothiazole.

In addition, the present invention is also directed to a novel method for the preparation of certain of the above-described triazolobenzoxazole and triazolobenzothiazole compounds.

DETAILED DESCRIPTION OF THE INVENTION—COMPOUNDS

A. Scope

The scope of compounds serving as active agent in accordance with the present invention is as defined hereinabove. Where the term "halo" is employed, it refers to fluorine, chlorine, bromine, and iodine, only. Those moieties defined herein as lower alkyl and alkyl (alone or as part of composite terms) and lower alkoxy can be branched- or straight-chain alkyl. Where $R^2$ represents di(lower alkyl of $C_1$–$C_3$)amino, the lower alkyl groups can be the same or different. In the instance of the salts, the term "phytologically-acceptable" is used to designate acids which do not in salt form produce phytotoxicity. The choice of the acid is otherwise not critical, although a given anion may in some instances exhibit special advantages, such as ready solubility, ease of crystallization, and the like. Representative and suitable acids include the following: hydrochloric, hydrobromic, hydriodic, sulfuric, phosphoric, nitric, acetic acid, trifluoroacetic acid, acrylic acid, o-aminobenzenesulfonic acid, bromoacetic acid, citric acid, cyclohexane-1,1-dicarboxylic acid, formic acid, maleic acid, malonic acid, oxalic acid, p-toluenesulfonic acid, methanesulfonic acid and the like.

B. Synthesis

The compounds to be employed in accordance with the present invention are prepared by a variety of synthetic methods. Several methods, however, are generally applicable.

A first method generally useful in the preparation of the compounds to be employed in accordance with the present invention is the cyclization of a 2-(2-acylhydrazino)benzoxazole or 2-(2-acylhydrazino)benzothiazole:

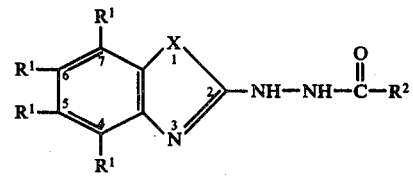

to the corresponding compound of Formula I. The reaction is useful for the preparation of compounds of Formula I wherein X represents oxygen or sulfur and $R^2$ represents hydrogen, alkyl as defined, cyclopropyl, trifluoromethyl, or

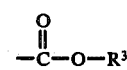

and $R^3$ represents lower alkyl of $C_1$–$C_3$. Where the identity of $R^2$ is otherwise, various other synthetic routes, discussed below, are preferred. In general, this synthetis route is useful regardless of the identity of $R^1$.

The desired cyclization is readily achieved by refluxing the 2-(2-acylhydrazino)benzoxazole or 2-(2-acylhydrazino)benzothiazole in phenol. Cyclization yields the desired product and water as by-product. Separation and if desired purification are carried out in conventional procedures.

The cyclization of 2-(2-acylhydrazino)benzothiazoles by refluxing in phenol is known in the prior art: see Reynolds and VanAllan, "The Synthesis of Polyazaindenes and Related Compounds," 24 *J. Org. Chem.* 1478 (1959). It has now been discovered that the cyclization of the 2-(2-acylhydrazino)benzoxazole and -benzothiazole compounds described above can be effected with polyphosphoric acid. Polyphosphoric acid is known as a cyclizing agent; see Popp and McEwen, "Polyphosphoric Acid as a Reagent in Organic Chemistry", 58 *Chemical Reviews* 321 (1958). However, its efficacy in the synthesis of compounds of Formula I is surprising in view of the comment in the Reynolds and VanAllan artical (footnote 5) that numerous reagents other than phenol did not effect ring closure of this type of compounds. As with phenol, the use of polyphosphoric acid results in preparation of the compounds of Formula I. However, the use of polyphosphoric acid is advantageous in that it gives good yields and permits ready separation of the desired product from the reaction mixture upon completion of the reaction.

Thus, the present improved method of synthesis is a method for the preparation of a compound of the formula

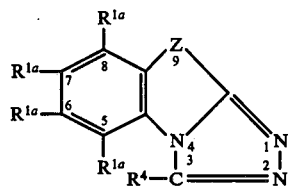

which method comprises reacting, at a reaction temperature of from 0° to 250°, a corresponding 2-(2-acylhydrazino)benzoxazole or benzothiazole of the formula

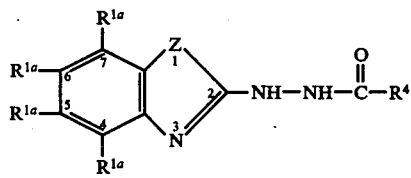

with polyphosphoric acid. In the above and succeeding formulae, each $R^{1a}$ independently represents hydrogen, halo, lower alkyl of $C_1$-$C_3$, lower alkoxy of $C_1$-$C_3$, or lower alkylthio of $C_1$-$C_3$; Z represents oxygen or sulfur; and $R^4$ represents hydrogen, alkyl of $C_1$-$C_{11}$, cyclopropyl, trifluoromethyl, or radical of the formula

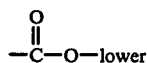

alkyl of $C_1$-$C_3$, subject to the limitations (1) that at least two $R^{1a}$'s or at least one $R^{1a}$ and $R^4$, represent hydrogen; and (2) that when both $R^4$ and the $R^{1a}$ substituent at the 5-position represent groups other than hydrogen, such groups together do not contain more than six carbon atoms.

In carrying out the reaction, the 2-(2-acylhydrazino)-benzoxazole or benzothiazole starting material is contacted with the polyphosphoric acid. An inert liquid can be used as a reaction medium, but since polyphosphoric acid is itself a liquid, it is preferred to use only polyphosphoric acid in excess. Condensation to the compound of Formula I occurs at a reaction temperature of from 0° to 250° C. Preferably, the 2-(2-acylhydrazino)benzoxazole or benzothiazole and polyphosphoric acid are mixed and the mixture heated to higher temperatures within the reaction, such as temperatures from 100° to 200° C. Some of the desired product is obtained at once upon the contacting of the reactants within the reaction temperature range; but higher yields are obtained by maintaining the mixture for a period of time, from several minutes to several hours or more.

Separation of the product is readily achieved by pouring the reaction into water and filtering off or extracting the product. Other conventional methods can also be used for separation and for purification where that is desired.

A second synthetic method generally applicable to the preparation of the compounds to be employed in accordance with the present invention is the reaction of a 2-hydrazinobenzoxazole or 2-hydrazinobenzothiazole;

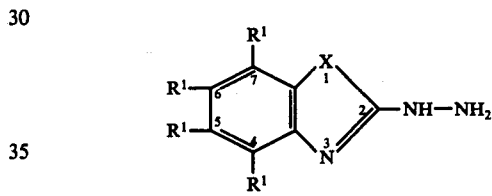

with an ortho ester of the formula

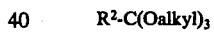

$R^2$-C(Oalkyl)$_3$

This synthetic route is useful for the preparation of those compounds of Formula I wherein X represents oxygen or sulfur and $R^2$ represents hydrogen, methyl, ethyl, or cyclopropyl. As in the first synthetic method, the identity of $R^1$ groups is not critical. The reaction consumes the reactants in equimolecular amounts, producing the desired compound and the corresponding alkanol as by-product. An inert liquid is conveniently employed as reaction medium. The reaction goes forward under a wide range of temperatures, such as from 25° to 200°, but better yields are more rapidly achieved by conducting the reaction at the reflux temperature of the reaction mixture. Separation, and, if desired, purification, are carried out in conventional procedures.

A third method generally useful in the preparation of the compounds to be employed in accordance with the present invention is the condensation of a 2-hydrazinobenzothiazole or benzoxazole:

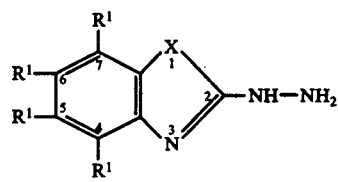

with an acid of the formula R$_2$—COOH. The reaction is useful for the preparation of those compounds of Formula I wherein X represents oxygen or sulfur and R$^2$ represents hydrogen, alkyl as defined, cyclopropyl, trifluoromethyl or

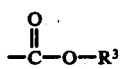

and R$^3$ represents lower alkyl of C$_1$–C$_3$. Where the identity of R$^2$ is otherwise, other synthetic routes are preferred. In general, this synthesis route is useful regardless of the identity of R$^1$.

To effect this condensation reaction, the reactants are contacted with one another. The reaction consumes the reactants in equimolecular amounts, producing the desired compound and water as by-product. Although an inert solvent can be employed, the acid reactant is typically a liquid and an excess thereof is more conveniently used. The reaction goes forward under a wide range of temperatures, but better yields are more rapidly achieved by conducting the reaction at the reflux temperature of the reaction mixture. Separation, and, if desired, purification, are accomplished in conventional procedures.

Various other synthetic methods are required for those compounds wherein R$^2$ represents certain moieties. Where R$^2$ represents —OH, the compounds are prepared by reacting a 2-hydrazinobenzoxazole or benzothiazole:

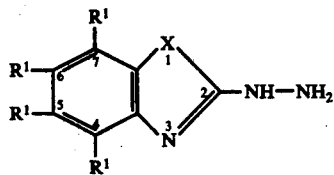

with urea. Likewise, where R$^2$ represents SH, the compounds are prepared by reacting the same precursor compounds with potassium hydroxide and carbon disulfide. In either case, subsequent alkylation converts the initial products to those compounds wherein R$^2$ represents lower alkoxy, lower alkylthio, allylthio, propynylthio, or benzylthio. Compounds wherein R$^2$ represents amino are prepared by reacting the same 2-hydrazinobenzoxazole or 2-hydrazinobenzothiazole with cyanogen bromide.

Yet other compounds to be employed in accordance with the present invention are derived from a cyclization product:

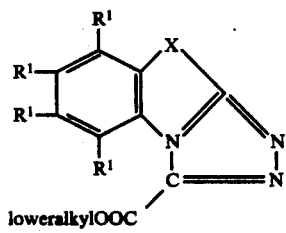

by conventional reactions. Included among such reactions are hydrolysis of the ester to the sodium or potassium salt (R$^2$ =

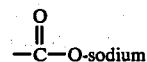

or potassium); and aminolysis of the ester to form the amide (R$^2$ = carbamoyl). Acylation of the 3—NH$_2$ compound yields the acetamido group (R$^2$ = acetamido) or other amides; and reduction of such amides yields substituted amine groups (R$^2$ = (lower alkyl of C$_1$–C$_3$)amino or di(lower alkyl of C$_1$–C$_3$)amino).

The R$^2$ = halo and thiocyanato compounds are obtained from the corresponding compound of Formula I wherein R$^2$ = H. This compound is reacted with a halogenating agent, such as an N-halosuccinimide. Other halogen derivatives not readily obtainable by N-halosuccinimide reaction can be obtained by known halogen exchange reactions, such as the Finkelstein reaction. The 3-halo compounds can also be employed as precursors to the 3-substituted amino, 3-lower alkoxy, and other 3-substituted compounds defined by Formula I. Thus, the 3-halo compound can be reacted with NaSCN to introduce the 3-thiocyanato group. Those compounds wherein R$^2$ represents halomethyl are readily prepared by reacting the corresponding compounds wherein R$^2$ represents methyl with a halogenating agent, and optionally converting by the Finkelstein reaction, as discussed above for the preparation of compounds where R$^2$ represents halogen. Those compounds wherein R$^2$ represents mono or di(lower alkyl of C$_1$–C$_3$)aminomethyl are prepared from the unsubstituted compound by the Mannich reaction. In the conduct of these numerous reactions, effecting the identity of the R$^2$ substituents, reference is directed to *Synthetic Organic Chemistry*, Wagner and Zook (John Wiley and Sons, Inc., New York, 1956); and to *Advanced Organic Chemistry*, Fieser and Fieser (Reinhold Publishing Co., New York, 1961).

The foregoing methods are useful for the preparation of products of Formula I essentially regardless of the identity of the R$^1$ substituent. Generally, it is preferred that substituents of the specified identity already be present on the starting compound. Sometimes, however, it is preferred to conduct the foregoing methods with a starting compound bearing a different substituent than that ultimately desired, and then convert the substituent on the resulting triazolobenzoxazole or triazolobenzothiazole to the desired substituent. Also, a compound bearing an additional substituent, notably a carboxyl, can be employed and then the carboxyl can be removed by decarboxylation. Reference is made to *Synthetic Organic Chemistry*, supra, and to *Advanced Organic Chemistry*, supra.

The compounds of Formula I wherein X represents

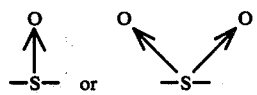

are readily prepared by oxidation of the corresponding benzothiazole (X=S) compound.

The compounds defined by Formula I form acid addition salts with acids. The salts are prepared in conventional procedures, by the reaction in a suitable solvent of the compound of Formula I as a free base with the desired acid. Separation and, if desired, purification, are carried out in established procedures. Generally, such salts are 1:1 salts. However, certain of the compounds of Formula I—those wherein $R^1$ or $R^2$ is or comprises an amino or substituted amino group—form salts of two or more acid moieties per moiety of the compound of Formula I. Also, in the case of dibasic or polybasic acids, salts may form of two or more molecules of compound of Formula I per molecule of acid. Such di or poly salts are also within the scope of the present invention. In order that the salts be useful in the practice of the present invention, phytologically acceptable salts are preferred.

The following examples illustrate the synthesis of the compounds to be employed in accordance with the present invention.

EXAMPLE 1 s-Triazolo(3,4-b)benzothiazole

2-Hydrazinobenzothiazole (125 grams; 0.76 mole), ethyl orthoformate (112.4 grams, 0.76 mole), and 2 liters of xylene were heated together with stirring in a three-necked 5-liter flask. An 8-inch column with a condenser was placed in one neck. The reaction was heated to 105° C. and soon all the solid had gone into solution and the solution turned red. Ethanol began to distill from the reaction and about 125 milliliters of it was collected before the reaction was stopped and allowed to cool to room temperature. The yellow precipitate was collected and triturated with diethyl ether. The s-triazolo(3,4-b)benzothiazole product thus obtained was recrystallized from chloroform, m.p. 174.5°–7° C.

EXAMPLE 2

3-Trifluoromethyl-s-triazolo(3,4-b)benzothiazole 2-(2-(Trifluoroacetyl)hydrazino)benzothiazole (17.8 grams) was mixed with phenol (44.5 grams) and refluxed for 24 hours. The reaction mixture was then steam distilled to remove the phenol, and the oil remaining was extracted with chloroform/water. The chloroform was subsequently stripped and the remaining material, the desired 3-trifluoromethyl-s-triazolo(3,4-b)benzothiazole product, recrystallized from ethyl acetate. The product so obtained melted at 140°–1° C.

EXAMPLE 3 s-Triazolo(3,4-b)benzothiazole-3-thiol

2-Hydrazinobenzothiazole (300 grams), potassium hydroxide (100 grams), and 225 milliliters of carbon disulfide were refluxed for 60 hours in 5500 milliliters of ethanol. A light yellow solid began precipitating out shortly after the beginning of reflux. The solid was collected by filtration and dissolved in water to which 1500 milliliters of 0.5N hydrochloric acid were added. The mixture thickened; the desired s-triazolo(3,4-b)benzothiazole-3-thiol product was collected by filtration, m.p., 242° C.

EXAMPLE 4

3-Amino-s-triazolo(3,4-b)benzothiazole hydrobromide

2-Hydrazinobenzothiazole (275 grams; 1.64 mole) was suspended in 2.5 liters of methanol and cyanogen bromide (174 grams; 1.64 moles) added in portions with stirring. After all the cyanogen bromide had been added, the reaction mixture thickened and the temperature began to rise. The reaction mixture was cooled with an ice bath and one-half of the contents removed and transferred to another flask. About 1 liter of methanol was added to each of the halves and each heated with stirring, to reflux. At reflux temperature, a clear red solution was observed and soon a light brown precipitate began to form. Refluxing was continued for 5 hours. The reaction mixture was then cooled and most of the solvent removed on a steam bath. Diethyl ether was added with further cooling, to produce a yellow precipitate, the desired 3-amino-s-triazolo(3,4-b)benzothiazole hydrobromide. It was collected and washed with petroleum ether. The product was purified by dissolving it in a minimal amount of boiling water and filtering the insolubles from solution. The filtrate was then cooled, resulting in reprecipitation of the product. After recrystallization from methanol/diethyl ether and then methanol alone, the product melted at 260°–2° C.

EXAMPLE 5 s-Triazolo(3,4-b)benzothiazol-3-ol

2-Hydrazinobenzothiazole (100 grams) and urea (100 grams) were fused on an oil bath at about 180° C. for about an hour, by which time the molten material had solidified and evolution of ammonia had ceased. The solid thus obtained, the desired s-triazolo(3,4-b)benzothiazol-3-ol, was recrystallized twice from methanol, m.p., 235° C.

EXAMPLE 6

3-Methylthio-s-triazolo(3,4-b)benzothiazole s-Triazolo(3,4-b)benzothiazole-3-thiol (238 grams; 1.14 mole); sodium hydroxide (50 grams; 1.25 mole) and methyl iodide (325 grams; 2.30 mole) were mixed together in 2500 milliliters of water, and the mixture heated to reflux and refluxed for about 45 minutes. The heat was then increased and the reflux condenser removed to allow the excess methyl iodide to evaporate. The solid material that had formed, the desired 3-methylthio-s-triazolo(3,4-b)benzothiazole, was collected on a filter. The water solution was cooled. The collected solid was dissolved in ethyl acetate (about 2500 ml.) and recrystallized. Another crop of the desired product crystallized out of the water. The combined crop melted at 129°–30° C.

EXAMPLE 7

3-Bromo-s-triazolo(3,4-b)benzothiazole s-Triazolo(3,4-b)benzothiazole (6.4 grams; 0.0366 mole) was slurried with 200 milliliters of carbon tetrachloride, with stirring, at room temperature, and then heated. N-Bromosuccinimide (6.8 grams; 0.0366 mole plus 5 percent) was added and the solution refluxed and a pinch of azobisisobutylnitrile added to initiate the reaction. Subsequently the reaction mixture was filtered to separate blackish crystals, which were washed with carbon tetrachloride. The carbon tetrachloride was removed by evaporation, to yield a purple solid. This was chromatographed on a column packed with silica gel and eluted with ethyl acetate. The second portion was analyzed by elemental analysis and NMR, which confirmed its identity as the expected 3-bromo-s-triazolo(3,4-b)benzothiazole, m.p., 166°–7° C.

EXAMPLE 8

3-Chloro-s-triazolo(3,4-b)benzothiazole 9,9-dioxide

3-Chloro-s-triazolo(3,4-b)benzothiazole (10.5 grams) was dissolved in 100 milliliters of methylene chloride and cooled to 0° C. m-Chloroperbenzoic acid (10.2 grams) was added portionwise, with stirring, in 125 milliliters of methylene chloride. The reaction mixture was then refluxed for an hour, another 10.2 grams of m-chloroperbenzoic acid in 125 milliliters of methylene chloride added, and the reaction mixture refluxed for a second hour. The reaction mixture was taken to dryness in vacuo. The reaction mixture was then run through a column of silica gel and eluted, initially with benzene, which was then changed gradually to ethyl acetate. The first portion collected was confirmed by IR, NMR, elemental analysis, and mass spectroscopy as the desired 3-chloro-s-triazolo(3,4-b)benzothiazole 9,9 dioxide product, m.p. 218°–20° C.

EXAMPLE 9

3-Methyl-s-triazolo(3,4-b)benzothiazole p-toluenesulfonate

3-Methyl-s-triazolo(3,4-b)benzothiazole (2 grams) was dissolved in 50 milliliters of ethanol. To this solution, 2 grams of p-toluenesulfonic acid were added, with stirring. After thorough mixing, the reaction mixture was heated to 90° C. and maintained at 90° C. for 1 hour. Solvent was thereafter removed under reduced pressure, yielding the desired salt as a solid. It was recrystallized from ethanol, m.p., 163°–4° C. NMR confirmed its identity. After a second recrystallization from ethanol, elemental analysis showed the following:

Analysis, Calc.: C, 53.17; H, 4.18; N, 11.73. Found: C, 53.29; H, 4.19; N, 11.71.

EXAMPLE 10

3-(Trifluoromethyl)-s-triazolo(3,4-b)benzothiazole 1-(2-Benzothiazolyl)-2-(trifluoroacetyl)hydrazine (2.5 grams) was slurried with 75 milliliters of polyphosphoric acid and the slurry heated to 160° C. for 4 hours. The reaction mixture was then poured over ice, causing the precipitation of the desired 3-(trifluoromethyl)-s-triazolo(3,4-b)benzothiazole product. It was separated by filtration and dissolved in chloroform, and the solution filtered through charcoal. The chloroform was then removed by evaporation under reduced pressure, yielding a purified product, which, after recrystallization from ethanol, melted at 139°–41° C.

EXAMPLE 11

3,5-Dimethyl-s-triazolo(3,4-b)benzothiazole

A solution of 6.1 grams of 2-hydrazino-4-methylbenzothiazole (0.034 mole) and 6.4 grams of triethyl orthoacetate (0.04 mole) in 200 milliliters of xylene was brought to reflux temperature over a period of 5 hours and thereafter refluxed for 96 hours. The reaction mixture was then concentrated to one-fourth of the original volume and allowed to cool to room temperature. The 3,5-dimethyl-s-triazolo(3,4-b)benzothiazole product was separated by filtration, 4 grams, m.p., 196°–8° C.

Analysis Calc.: C, 59.09; H, 4.46; N, 20.67. Found: C, 59.10; H, 4.47; N, 20.73.

EXAMPLE 12

5,6-Dimethyl-s-triazolo(3,4-b)benzothiazole

A solution of 12 milliliters of formic acid (97–100 percent) and 3.5 grams of 2-hydrazino-4,5-dimethylbenzothiazole was refluxed for 24 hours with stirring. The reaction mixture was then cooled to room temperature and poured into water. The 5,6-dimethyl-s-triazole(3,4-b)benzothiazole compound precipitated and was separated by filtration, 2.6 grams, m.p. 226–8° C.

Analysis, Calc.: C, 59.09; H, 4.46; N, 20.67. Found: C, 58.88; H, 4.17; N, 20.39.

EXAMPLE 13

3-(Dimethylaminomethyl)-s-triazolo(3,4-b)-benzothiazole hydrochloride

A mixture of s-triazolo(3,4b)benzothiazole (7.5 grams; 0.042 mole), paraformaldehyde (2.52 grams), dimethylamine hydrochloride (4.48 grams), and isoamyl alcohol (15.5 milliliters) was refluxed for 7 hours. The reaction mixture was then cooled overnight; the desired 3-(dimethylaminomethyl)-s-triazolo(3,4-b)-benzothiazole hydrochloride product precipitated and was separated by filtration. It was subsequently washed with ether and then recrystallized from ethanol/ether, m.p., 245–6° C.

EXAMPLES 14–49

Other representative compounds, prepared in the methods described and exemplified hereinabove using analogous starting materials, are the following:

3-Amino-s-triazole(3,4-b)benzoxazole hydrochloride, m.p., 220° C. (dec.)
s-Triazolo(3,4-b)benzoxazole, m.p., 162–3° C.
3-Ethylthio-s-triazolo(3,4-b)benzothiazole, m.p., 105–7° C.
3-(2-Propynylthio)-s-triazolo(3,4-b)benzothiazole, m.p., 165–6° C.
3-(Propylthio)-s-triazolo(3,4-b)benzothiazole, m.p., 81–3° C.
3-Ethyl-s-triazolo(3,4-b)benzothiazole, m.p., 115–6° C.
3-Methyl-s-triazolo(3,4-b)benzothiazole, m.p., 146–8° C.
3-Methyl-s-triazolo(3,4-b)benzoxazole, m.p., 175–8° C.
3-Dimethylaminomethyl-s-triazolo(3,4-b)benzothiazole hydrochloride, m.p., 245–6° C.
3,5,6-Trimethyl-s-triazolo(3,4-b)benzothiazole, m.p., 246–8° C.
3,6,7-Trimethyl-s-triazolo(3,4-b)benzothiazole, m.p., 243–5° C.
3-Chloro-5-methyl-s-triazolo(3,4-b)benzothiazole, m.p., 170–2° C. (dec.)
2-Undecy-s-triazolo(3,4-b)benzothiazole, m.p., 68°–70° C.
3-Methyl-5-fluoro-s-triazolo(3,4-b)benzothiazole, m.p., 141–2° C.
5-Fluoro-s-triazolo(3,4-b)benzothiazolo, m.p., 172–3° C.
5-Ethyl-s-triazolo(3,4-b)benzothiazole, m.p., 152–3° C.
5,7-Dichloro-s-triazolo(3,4-b)benzothiazole, m.p., 246–8° C.
3-Amino-5-chloro-s-triazolo(3,4-b)benzothiazole hydrobromide, m.p., 240–2° C.
3-Chloromethyl-s-triazolo(3,4-b)benzothiazole, m.p., 177–9° C.
3-Chloro-s-triazolo(3,4-b)benzothiazole, m.p., 149–51° C.
5-Methoxy-s-triazolo(3,4-b)benzothiazole, m.p., 178–80° C.
5-Chloro-s-triazolo(3,4-b)benzothiazole, m.p., 186–7.5° C.

6,7-Dimethyl-s-triazolo(3,4-b)benzothiazole, m.p., 272-4° C.
3,5-Dichloro-s-triazolo(3,4-b)benzothiazole, m.p., 178-82° C.
7-Methoxy-s-triazolo(3,4-b)benzothiazole, m.p., 178-81.5° C.
3-Acetamido-s-triazolo(3,4-b)benzothiazole, m.p., 270-2° C.
5-Methyl-s-triazolo(3,4-b)benzothiazole, m.p., 184-5° C.
3-Methoxy-s-triazolo(3,4-b)benzothiazole, m.p., 155-6° C.
7-Ethoxy-s-triazolo(3,4-b)benzothiazole, m.p., 162-3° C.
s-Triazolo(3,4-b)benzothiazol-3-yl thiocyanate, m.p., 209-10° C.
s-Triazolo(3,4-b)benzothiazole-3-carboxamide, m.p., 262-5° C.
3-Pentyl-s-triazolo(3,4-b)benzothiazole, m.p., 95-6° C.
3-Isopropyl-s-triazolo(3,4-b)benzothiazole, m.p., 78°-80° C.
3-Propyl-s-triazolo(3,4-benzothiazole, m.p., 129°-31° C.
3-Methyl-s-triazolo(3,4-b)benzothiazole hydrochloride, m.p., 239-40° C.
3-Methyl-s-triazolo(3,4-b)benzothiazole hemisulfate, m.p., 210-2° C.

EXAMPLES 50-75

Other representative compounds of Formula I are prepared as described in accordance with the foregoing teachings.

s-Triazolo(3,4-b)benzothiazole 9-oxide
3-Cyclopropyl-s-triazolo(3,4-b)benzothiazole
3-Methyl-s-triazolo(3,4-b)benzothiazole acetate
3-Methoxy-s-triazolo(3,4-b)benzoxazole
s-Triazolo(3,4-b)benzoxazole phosphate
3-Methyl-s-triazolo(3,4-b)benzoxazole
3-Ethoxy-s-triazolo(3,4-b)benzothiazole
3-Propoxy-s-triazolo(3,4-b)benzoxazole hydrobromide
s-Triazolo(3,4-b)benzothiazole sulfate
3-Allylthio-s-triazolo(3,4-b)benzothiazole
3-(1-Propynylthio)-s-triazolo(3,4-b)benzoxazole
3-Benzylthio-s-triazolo(3,4-b)benzothiazole
3-Fluoro-5-methyl-s-triazolo(3,4-b)benzoxazole
3-Methylamino-s-triazolo(3,4-b)benzoxazole
3-Dimethylamino-s-triazolo(3,4-b)benzoxazole
3-Propylamino-s-triazolo(3,4-b)benzothiazole
Ethyl s-triazolo(3,4-benzothiazole-3-carboxylate
Sodium s-triazolo(3,4-b)benzoxazole-3-carboxylate
3,8-Dimethyl-s-triazolo(3,4-benzothiazole
5,6,8-Trichloro-s-triazolo(3,4-b)benzothiazole
3-Chloromethyl-s-triazolo(3,4-b)benzoxazole
Potassium s-triazolo(3,4-b)benzothiazole-3-carboxylate
s-Triazolo(3,4b)benzoxazole phosphate
3-Ethylaminomethyl-s-triazolo(3,4-b)benzoxazole
5-Methylthio-s-triazolo(3,4-b)benzothiazole
5-Ethylthio-s-triazolo(3,4-b)benzoxazole

DETAILED DESCRIPTION OF THE INVENTION

It has been discovered that the compounds of Formula I (hereinafter referred to as "triazolobenzoxazole and triazolobenzothiazole compounds") are adapted to be employed for the control of plant pathogens, including fungal organisms and bacterial organisms. Thus, the triazolobenzoxazole and triazolobenzothiazole compounds can be employed for the control of such organisms as crown gall, rice blast, bean rust, powdery mildew, anthracnose, and the like. The compounds are particularly suited for the control of fungal organisms, and give particularly good results in the control of rice blast.

The compounds can be employed and are effective when utilized in any of a number of embodiments. In accordance with prevalent practice, the compounds can be applied, and are effective against plant-pathogenic organisms when applied, to the foliage of plants susceptible to attack. In addition, the triazolobenzoxazole and triazolobenzothiazole compounds can be applied to seeds to protect the seeds and ensuing plants from the attack of plant-pathogenic organisms. Also, the compounds can be distributed in soil to control plant-pathogenic organisms. It has been found that many of the compounds are translocated through plants, so that in this last embodiment, control is achieved of foliage-attacking organisms as well as organisms which attack other plant parts.

Most broadly, the method of the present invention for the control of plant-pathogenic organisms comprises applying to a locus control of plant-pathogenic organisms comprises applying to a locus of the organisms an effective amount of one or more of the triazolobenzoxazole and triazolobenzothiazole compounds. The compounds can be used alone; but the present invention also embraces the employment of a liquid, powder, or dust composition containing one or more of the triazolobenzoxazole or triazolobenzothiazole compounds. Such compositions are adapted to be applied to living plants without substantial injury to the plants. In preparing such compositions, the triazolobenzoxazole and triazolobenzothiazole compounds can be modified with one or more of a plurality of additaments including organic solvents, petroleum distillates, water or other liquid carriers, surface active dispersing agents, and finely divided inert solids. In such compositions, the triazolobenzoxazole or triazolobenzothiazole compound can be present in a concentration from about 2 to 98 percent by weight. Depending upon the concentration in the composition of the triazolobenzoxazole or triazolobenzothiazole compound, such augmented compositions are adapted to be employed for the control of undesirable plant pathogens or employed as concentrates and subsequently diluted with additional inert carrier to produce the ultimate treating compositions. Preferred compositions are those comprising both a finely divided solid and a surface active agent.

The exact concentration of the triazolobenzoxazole or triazolobenzothiazole compounds employed in the composition for application to plant-pathogens and/or their habitats can vary provided an effective amount is applied either on the organism or its environment. The amount which is effective is dependent in part upon the susceptibility of the particular plant pathogen and upon the activity of the compound employed. In general, good results are obtained with liquid compositions containing from about 0.001 to 0.1 percent or more by weight of triazolobenzoxazole or triazolobenzothiazole compound. With dusts, good results are usually obtained with compositions containing from 0.5 to 5.0 percent or more by weight of triazolobenzoxazole or triazolobenzothiazole compound. In terms of acreage application, good controls of plant pathogens are obtained when the compounds are applied to plots of growing plants at a dosage of from 0.5 to 5.0 or more pounds per acre.

In the preparation of dust compositions, the triazolobenzoxazole and triazolobenzothiazole compounds can be compounded with any of the finely divided solids such as pyrophyllite, talc, chalk, gypsum, and the like. In such operations, the finely divided carrier is ground or mixed with the triazolobenzoxazole or triazolobenzothiazole compound or wet with a solution of the same in a volatile organic solvent. Similarly, dust compositions containing the products can be compounded with various solid surface active dispersing agents such as fuller's earth, bentonite, attapulgite, and other clays. Depending upon the proportions of ingredients, these dust compositions can be employed for the control of plant pathogens or employed as concentrates and subsequently diluted with an additional solid surface active dispersing agent or with pyrophyllite, chalk, talc, gypsum, and the like to obtain the desired amount of active ingredient in a composition adapted to be employed for the control of plant pathogens. Also, such dust compositions, when employed as concentrates, can be dispersed in water, with or without the aid of dispersing agents, to form spray mixtures.

Futher, the triazolobenzoxazole and triazolobenzothiazole compounds or a liquid or dust concentrate composition containing such compounds can be incorporated in intimate mixture with surface active dispersing agents such as non-ionic emulsifying agents to form spray compositions. Such compositions are readily employed for the control of plant-pathogens or can be dispersed in liquid carriers to form diluted sprays containing the toxicants in any desired amount. The choice of dispersing agents and amounts thereof employed are determined by the ability of the agents to facilitate the dispersion of the concentrate in the liquid carrier to produce the desired spray compositions.

Similarly, the triazolobenzoxazole and triazolobenzothiazole compounds can be compounded with a suitable water-immiscible organic liquid and a surface active dispersing agent to produce emulsifiable concentrates which can be further diluted with water and oil to form spray mixtures in the form of oil-water emulsions. In such compositions, the carrier comprises an aqueous emulsion, i.e., a mixture of water-immiscible solvent, emulsifying agent and water. Preferred dispersing agents which can be employed in these compositions are oil-soluble and include the non-ionic emulsifiers such as condensation products of alkylene oxides with the inorganic acids, polyoxyethylene derivatives of sorbitan esters, complex ether alcohols and the like. Suitable organic liquids which can be employed in the composition include petroleum oils and distillates, toluene, and synthetic organic oils. The surface active dispersing agents are usually employed in liquid compositions in the amount of from 0.1 to 20.0 percent by weight of the combined weight of the dispersing agent and active compound.

When operating in accordance with the present invention, the triazolobenzoxazole and triazolobenzothiazole compounds or a composition containing the compounds can be applied to the pathogens to be controlled, or to their habitats in any convenient fashion, e.g., by means of hand dusters or sprayers. Applications to the above-ground portions of plants conveniently can be carried out with power dusters, boom sprayers, high-pressure sprayers, and spray dusters. In large-scale operations, dusts or low-volume sprays can be applied from airplanes. In the use of the triazolobenzoxazole and triazolobenzothiazole compounds for the control of rice blast, specialized modes of application may be preferred, owing to the peculiar cultural conditions under which rice is grown. Such specialized methods include surface water application, soak treatment of plants to be transplanted, seed treatment, and the like; other methods will be obvious to those skilled in the art.

The following examples illustrate the utility of the triazolobenzoxazole and triazolobenzothiazole compounds for the control of plant pathogens and will enable those skilled in the art to practice the same.

EXAMPLES 76–98

Various of the triazolobenzoxazole and triazolobenzothiazole compounds to be employed in accordance with the present invention were evaluated for the control of *Colletotrichum lagenarium* (anthracnose) on cucumber. These evaluations were conducted in accordance with the following procedure.

In each individual evaluation, a 4-inch pot containing sterilized soil, with a layer of vermiculite on the surface, was seeded with four cucumber seeds and held under normal greenhouse conditions. The seedlings were thinned to two plants; about fifteen days after the seeding, the foliage was sprayed with a solution of the respective compound, permitted to dry, and then inoculated by spraying it with a water suspension of conidia of *Colletotrichum lagenarium*.

Each triazolobenzoxazole or triazolobenzothiazole compound was formulated in conventional procedures. Typically, each compound was formulated by dispersing it in a specified amount of cyclohexanone containing a small amount of a blend of two sulfonatenonionic surfactants, and then diluting with water to obtain an ultimate treating composition containing 400 parts of the given compound per million parts by weight of the ultimate composition, in addition to the cyclohexanone in a concentration of 0.67 percent and the surfactant blend in a concentration of 0.0353 percent.

The suspension of conidia was prepared by culturing the fungus in petri plates on orange juice agar at 24° C. for 14 days. The plates were then flooded with distilled water and the surface scraped. The resulting aqueous suspension from four plates was filtered through cheesecloth, brought up to a volume of 50 milliliters, and used for spraying plants in about 35 pots.

After the plants had been inoculated, they were placed in a moist chamber at 18° C. for 48 hours, then removed and held for about 9 days under normal greenhouse conditions, and then evaluated for control of anthracnose.

In each evaluation, there was a control, based on treatment by an aqueous control solution containing cyclohexanone and the surfactant blend in the same respective concentrations.

The results of the evaluations were as set forth in the following table, using the following disease rating system:
 1—severe
 2—moderately severe
 3—moderate
 4—slight
 5—no disease In the control pots, there was uniformly a heavy infestation of anthracnose on the cucumber plants. Phytotoxicity was uniformly non-existent or only slight in degree, except that substantial phytotoxicity was observed on the plants treated with 5-methyl-s-triazolo(3,4-b)benzothiazole.

TABLE 1
CONTROL OF ANTHRACNOSE

| Name of Compound | Disease Rating |
|---|---|
| 3-Pentyl-s-triazolo(3,4-b)benzothiazole | 4+ |
| 3-Trifluoromethyl-s-triazolo(3,4-b)benzothiazole | 5 |
| 3-Chloro-s-triazolo(3,4-b)benzothiazole-9,9-dioxide | 4− |
| s-Triazolo(3,4-b)benzothiazole-3-thiol | 4+ |
| 3-Propyl-s-triazolo(3,4-b)benzothiazole | 3− |
| 3,5-Dichloro-s-triazolo(3,4-b)benzothiazole | 4+ |
| 3-Methylthio-s-triazolo(3,4-b)benzothiazole | 5 |
| s-Triazolo(3,4-b)benzothiazole | 5 |
| s-Triazolo(3,4-b)benzoxazole | 4 |
| 3-Ethylthio-s-triazolo(3,4-b)benzothiazole | 5 |
| 3-Propylthio-s-triazolo(3,4-b)benzothiazole | 5 |
| 1-Ethyl-s-triazolo(3,4-b)benzothiazole | 5 |
| 3-Methyl-s-triazolo(3,4-b)benzothiazole | 4+ |
| 3-Methyl-s-triazolo(3,4-b)benzoxazole | 4+ |
| 3-Chloro-s-triazolo(3,4-b)benzothiazole | 4+ |
| 3-Bromo-s-triazolo(3,4-b)benzothiazole | 4+ |
| 5-Methoxy-s-triazolo(3,4-b)benzothiazole | 3 |
| 5-Chloro-s-triazolo(3,4-b)benzothiazole | 4+ |
| 6,7-Dimethyl-s-triazolo(3,4-b)benzothiazole | 3+ |
| 7-Methoxy-s-triazolo(3,4-b)benzothiazole | 3 |
| 5-Methyl-s-triazolo(3,4-b)benzothiazole | 5 |
| 3-Methoxy-s-triazolo(3,4-b)benzothiazole | 5 |
| s-Triazolo(3,4-b)benzothiazol-3-yl thiocyanate | 3 |

EXAMPLES 99–106

Representative triazolobenzoxazole and triazolobenzthiazole compounds were also evaluated for the control of the causative pathogen of crown gall disease (*Agrobacterium tumefaciens*) on tomato plants. Each such evaluation was conducted in accordance with the following procedure.

Three tomato seeds were planted in sand in 4-inch plastic pots, and later thinned to two plants. Meanwhile, an inoculum of *Agrobacterium tumefaciens* was grown in test tubes on homemade potato dextrose agar. The cultures were then flooded with sterile water to make the required amount of bacterial suspensions, which was used to inoculate the tomato seedlings at about 4 weeks following seeding. The inoculation was carried out by dipping a small insect mounting needle into the bacterial suspension and then passing the needle through the stem of each tomato plant. The plants were then removed from the sand and the roots of each placed in an aqueous solution in a large test tube, the solution containing the test chemical in a concentration of 40 ppm., 0.067 percent cyclohexanone, and 0.00353 percent surfactant, and sodium chloride in a concentration of 0.85 percent. The plants were held under normal greenhouse conditions, with daily aeration, for about 10 days. At this time, each plant was observed to determine the presence of crown gall disease.

A control was conducted by placing two inoculated plants in a solution in a separate test tube, which solution contained all ingredients except test chemical. This test tube was held and treated in all other respects exactly like the tubes containing the treated plants.

The results of the evaluations are presented in the following table, employing the same rating scales as in previous examples. All control plants showed extensive symptoms of crown gall disease. Phytotoxicity was in all instances either non-existent or of only slight degree, except that substantial phytotoxicity was noted on the plants treated with 5-methoxy-s-triazolo-(3,4-b)benzothiazole.

TABLE 2
CONTROL OF CROWN GALL

| Name of Compound | Disease Rating |
|---|---|
| 3-Methylthio-s-triazolo(3,4-b)benzothiazole | 5 |
| s-Triazolo(3,4-b)benzothiazole | 3 |
| 3-(Propylthio)-s-triazolo(3,4-b)benzothiazole | 5 |
| 5-Methoxy-s-triazolo(3,4-b)benzothiazole | 5 |
| 7-Methoxy-s-triazolo(3,4-b)benzothiazole | 3− |
| 3-Methoxy-s-triazolo(3,4-b)benzothiazole | 3− |
| 7-Ethoxy-s-triazolo(3,4-b)benzothiazole | 3− |
| s-Triazolo(3,4-b)benzothiazole-3-carboxamide | 3 |

EXAMPLES 107–112

Various of the present triazolobenzoxazole and triazolobenzothiazole compounds were evaluated for the control of powdery mildew (*Erysiphe polygoni*) on beans. The evaluations were conducted as follows.

In 4-inch pots of soil, four bean seeds were planted, and later thinned to two seedlings. On the tenth day following seeding, a test chemical was applied to the young plants in the form of a composition formulated as described hereinabove in Examples 76–98. The treated plants were then placed near to and beneath other plants heavily infested with powdery mildew, to assure infestation of the treated plants by natural air currents. In this relationship, the plants were held under normal greenhouse conditions for about 7 to 10 days, at which time the plants were observed to determine the presence of symptoms of powdery mildew disease. A control was run with each evaluation; the control consisted of a group of four plants treated with a solvent-emulsifier solution containing no test chemical, also as described in Examples 76–98. The results are as set forth in the following table, employing the same rating scales as in previous examples. In the controls, the bean plants uniformly showed heavy infestation by powdery mildew. Phytotoxicity was in all instances either non-existent or of only slight degree.

TABLE 3
CONTROL OF POWDERY MILDEW

| Name of Compound | Disease Rating |
|---|---|
| s-Triazolo(3,4-b)benzothiazole-3-thiol | 3− |
| 3-Ethylthio-s-triazolo(3,4-b)benzothiazole | 3 |
| 6,7-Dimethyl-s-triazolo(3,4-b)benzothiazole | 5 |
| s-Triazolo(3,4-b)benzothiazole-3-carboxamide | 3 |
| 3-Propyl-s-triazolo(3,4-b)benzothiazole | 3 |
| 3,5-Dichloro-s-triazolo(3,4-b)benzothiazole | 5 |

EXAMPLES 113–149

Various triazolobenzoxazole and triazolobenzothiazole compounds were evaluated for the control of rice blast (*Piricularia oryzae*). The evaluation was carried out in accordance with the following procedure: a soil was prepared by blending together equal parts of masonry sand and shreaded topsoil. The soil was placed in 4-inch pots and thickly seeded with rice seed. The seeded pots were then held under typical greenhouse conditions for about 2 weeks, by which time there were thick stands of rice seedlings in each pot.

Also, an aqueous suspension of conidia of the rice blast fungus was prepared. The fungus was cultured in petri dishes on rice polish agar at 28° C. After 8 days, each plate was flooded with 20 milliliters of distilled water and the culture surface was scraped with a rubber policeman to separate conidia.

In each instance, a treating solution prepared as described in Examples 76–98 was sprayed onto the leaf surfaces of the rice stand in one pot, allowed to dry, and the foliage then inoculated with the aqueous suspension of conidia of the rice blast organism. In each instance, the treating solution contained 400 parts of the compound per million parts of ultimate solution, by weight. The pot was placed in a moist chamber at 18° C. and held there for 48 hours, then returned to the greenhouse and held under typical greenhouse conditions for 6 days. At this time, readings were made in accordance with the same disease rating scale reported in preceding examples. The control was conducted as follows: Pots of rice seedlings were sprayed with an aqueous solution of cyclohexanone and the same blend of two sulfonate-nonionic surfactants but containing no compound. Otherwise, the pots were treated identically.

The results of the evaluations are as reported in the following table. Not all of these evaluations were conducted simultaneously. In all tests, however, the untreated control pots showed extensive symptoms of rice blast. Generally, no phytotoxicity was observed; however, on a few of the treated pots, there was slight phytotoxicity.

TABLE 4
CONTROL OF RICE BLAST

| Name of Compound | Disease Rating |
|---|---|
| 3-Trifluoromethyl-s-triazolo(3,4-b)benzothiazole | 4 |
| s-Triazolo(3,4-b)benzothiazol-3-thiol | 4 |
| 3-Amino-s-triazolo(3,4-b)benzothiazole hydrobromide | 4 |
| s-Triazolo(3,4-b)benzothiazol-3-ol | 5 |
| 3-Methylthio-s-triazolo(3,4-b)benzothiazole | 4+ |
| s-Triazolo(3,4-b)benzothiazole | 4+ |
| 3-Amino-s-triazolo(3,4-b)benzoxazole hydrochloride | 3 |
| s-Triazolo(3,4-b)benzoxazole | 4+ |
| 3-Ethylthio-s-triazolo(3,4-b)benzothiazole | 3 |
| 3-(2-Propynylthio)-s-triazolo(3,4-b)benzothiazole | 3+ |
| 3-(Propylthio)-s-triazolo(3,4-b)benzothiazole | 3+ |
| 3-Methyl-s-triazolo(3,4-b)benzothiazole | 4+ |
| 3-Methyl-s-triazolo(3,4-b)benzoxazole | 5 |
| 3-Chloro-s-triazolo(3,4-b)benzothiazole | 5 |
| 3-Bromo-s-triazolo(3,4-b)benzothiazole | 4+ |
| 5-Methoxy-s-triazolo(3,4-b)benzothiazole | 4+ |
| 5-Chloro-s-triazolo(3,4-b)benzothiazole | 5 |
| 6,7-Dimethyl-s-triazolo(3,4-b)benzothiazole | 4+ |
| 7-Methoxy-s-triazolo(3,4-b)benzothiazole | 3+ |
| 3-Acetamido-s-triazolo(3,4-b)benzothiazole | 4 |
| 5-Methyl-s-triazolo(3,4-b)benzothiazole | 5 |
| 3-Methoxy-s-triazolo(3,4-b)benzothiazole | 3+ |
| 7-Ethoxy-s-triazolo(3,4-b)benzothiazole | 3 |
| s-Triazolo(3,4-b)benzothiazol-3-yl thiocyanate | 3 |
| s-Triazolo(3,4-b)benzothiazole-3-carboxamide | 3− |
| 3-Chloro-s-triazolo(3,4-b)benzothiazole 9,9-dioxide | 4+ |
| 3-Propyl-s-triazolo(3,4-b)benzothiazole | 4 |
| 3,5-Dichloro-s-triazolo(3,4-b)benzothiazole | 3 |
| 3-Pentyl-s-triazolo(3,4-b)benzothiazole | 4+ |
| 3-Chloro-5-methyl-s-triazolo(3,4-b)benzothiazole | 4+ |
| 3-Methyl-5-fluoro-s-triazolo(3,4-b)benzothiazole | 3+ |
| 5-Fluoro-s-triazolo(3,4-b)benzothiazole | 4 |
| 5-Ethyl-s-triazolo(3,4-b)benzothiazole | 4 |
| 5,7-Dichloro-2-triazolo(3,4-b)benzothiazole | 3 |
| 3-Amino-5-Chloro-s-triazolo(3,4-b)benzothiazole hydrobromide | 3 |
| 3-Dimethylaminomethyl-s-triazolo(3,4-b)benzothiazole hydrochloride | 4− |
| 3-Chloromethyl-s-triazolo(3,4-b)benzothiazole | 3− |

EXAMPLES 150–153

Several other of the compounds to be employed in accordance with the present invention were evaluated for the control of rice blast. The evaluations were conducted in the same procedures as those reported in Examples 113–149 with these differences: several evaluations were conducted with each compound, and the concentrations of the respective compound were 250, 500, and 1000 parts per million. The results were as reported in the following table.

TABLE 5
CONTROL OF RICE BLAST

| Name of Compound | Conc. in Treating Solution (ppm.) | Disease Rating |
|---|---|---|
| 3-Methyl-s-triazolo(3,4-b)benzothiazole p-toluenesulfonate | 1000 | 5 |
|  | 500 | 4+ |
|  | 250 | 5 |
| 3-Methyl-s-triazolo(3,4-b)-benzothiazole hemisulfate | 1000 | 5 |
|  | 500 | 5 |
|  | 250 | 5 |
| 3-Undecyl-s-triazolo(3,4-b)-benzothiazole | 1000 | 3 |
|  | 500 | 3− |
|  | 250 | 4+ |
| 3-Methyl-s-triazolo(3,4-b)-benzothiazole hydrochloride | 1000 | 5 |
|  | 500 | 5 |
|  | 250 | 2 |

EXAMPLES 154–159

Certain of the triazolobenzoxazole and triazolobenzothiazole compounds to be employed in accordance with the present invention were also evaluated for control of rice blast when applied to the soil prior to planting. In these evaluations, a quantity of the respective compound was dissolved in ethanol, the solution sprayed with a DeVilbiss atomizer onto soil rotating in a drum, and the soil thus treated placed in 4-inch round pots having no drainage holes. The procedures were such as to constitute a specified number of pounds of the compound per acre—25, 12.5, 6.25, 5.0, 2.5, or 1.25 pounds per acre. The pots were then seeded to rice (variety, Nato) and held under typical greenhouse conditions for 2 weeks, at which time the rice seedlings were inoculated with conidia of Piricularia oryzae, the preparation and inoculation as described in the preceding examples, and held in a moist chamber at 18° C. for 48 hours. The pots were then removed and again held under greenhouse conditions for another 5 days. At this time, observations for disease severity were made; results are as reported below using the rating scale of preceding examples.

There were three replications per test and additionally a control utilizing soil treated only with an aqueous solution of the same concentration of ethanol. In the control plots, there were extensive symptoms of rice blast disease.

TABLE 6
CONTROL OF RICE BLAST, PRE-PLANT SOIL INCORPORATED APPLICATION

| Compound | Rate of Application of Compound in Pounds Per Acre | Disease Rating |
|---|---|---|
| s-Triazolo(3,4-b)benzothiazole | 25.0 | 4 |
|  | 12.5 | 3+ |
|  | 6.25 | 2+ |
| 3-Methyl-s-triazolo(3,4-b)benzothiazole | 25.0 | 3+ |
|  | 12.5 | 4+ |
|  | 6.25 | 2+ |
| 3-Methyl-s-triazolo(3,4-b)benzoxazole | 25.0 | 4+ |
|  | 12.5 | 3 |
|  | 6.25 | 3− |
| 3-Chloro-s-triazolo(3,4-b)benzothiazole | 25.0 | 5 |
|  | 12.5 | N.T. |
|  | 6.25 | N.T. |
| 5-Chloro-s-triazolo(3,4-b)benzothiazole | 25.0 | 5 |
|  | 12.5 | 5 |
|  | 6.25 | 4+ |
|  | 5.0 | 5 |
|  | 2.5 | 4+ |

TABLE 6-continued
CONTROL OF RICE BLAST,
PRE-PLANT SOIL INCORPORATED APPLICATION

| Compound | Rate of Application of Compound in Pounds Per Acre | Disease Rating |
|---|---|---|
| 5-Methyl-s-triazolo(3,4-b)benzo-thiazole | 1.25 | 3 |
|  | 25.0 | 5 |
|  | 12.5 | 4+ |
|  | 6.25 | 4+ |
|  | 5.0 | 4+ |
|  | 2.5 | 3 |

*N.T. = Not tested

EXAMPLES 160–163

Various of the triazolobenzoxazole and triazolobenzothiazole compounds to be employed in accordance with the present invention were evaluated for control of rice blast (*Piricularia oryzae*) when applied to the surface of water-saturated soil in which rice was growing.

Rice (variety, Nato) was seeded in 4-inch round pots having no drainage holes. The soil was maintained in water-saturated condition throughout the test which was conducted under greenhouse conditions.

About 14 days after seeding, the seedlings were treated. Treatment was made by pouring onto the surface of soil in each pot a treating solution prepared as described in Examples 154–159. On the third day following treatment, the plants were inoculated with a pathogen suspension prepared as described in Examples 113–149 and placed in a moist chamber at 18° C. for 48 hours. The plants were then returned to normal greenhouse conditions and held for 5 days, at which time they were examined for the presence, and if present, degree of severity, of symptoms of rice blast.

Three replicates were run for each test. A control was also conducted for each test; the control consisted of usage of an aqueous solution containing 0.5 percent of ethanol, only. The results of the evaluations are reported in the following table. Control pots uniformly showed extensive rice blast disease symptoms.

TABLE 7
CONTROL OF RICE BLAST,
SOIL SURFACE APPLICATION

| Compound | Rate of Application of Compound in Pounds per Acre | Disease Rating |
|---|---|---|
| 3-Chloro-s-triazolo(3,4-b)benzo-thiazole | 25.0 | 4+ |
|  | 12.5 | 4+ |
|  | 6.25 | 3+ |
| 5-Chloro-s-triazolo(3,4-b)benzo-thiazole | 25.0 | 5+ |
|  | 12.5 | 4+ |
|  | 6.25 | 5 |
|  | 5.0 | 4+ |
|  | 2.5 | 4 |
|  | 1.25 | 4− |
| 5-Methyl-s-triazolo(3,4-b)benzo-thiazle | 25.0 | 4+ |
|  | 12.5 | 4 |
|  | 6.25 | 4 |
|  | 5.0 | 4− |
|  | 2.5 | 3 |
|  | 1.25 | 3− |
| s-Triazolo(3,4-b)benzothiazole | 25 | 4+ |
|  | 12.5 | 4− |
|  | 6.25 | 3− |

EXAMPLES 164–167

Various of the present triazolobenzothiazole compounds were evaluated for their efficacy in controlling rice blast when applied to the rice seed, by means of a seed soak.

The respective compound to be evaluated was dissolved in ethanol and diluted with water containing 0.1 percent of polyoxyethylene sorbitan monolaurate to obtain a treating solution containing the subject compound in a concentration of 250 parts of compound per million parts of total composition. All solutions uniformly contained 0.5 percent of ethanol and approximately 0.1 percent of the polyoxyethylene sorbitan monolaurate.

Twenty milliliters of each solution were placed in a separate 125-milliliter Erlenmeyer flask and 20 cc. (about 12.5 grams) of rice seed added (variety, Nato). Each flask was stoppered and shaken for 48 hours, at which time the rice was drained and rinsed with tap water.

The treated seed was thereafter planted in 4-inch square pots and held under typical greenhouse conditions. When the emerging rice seedlings had reached a height of 3 to 4 inches (about 14 days after seeding) they were inoculated with a fungal suspension of *Piricularia oryzae* (rice blast) prepared as in Examples 113–149. The plants were then incubated in a moist chamber at 18° C. for 48 hours, after which they were returned to the greenhouse and held for about 5 days. They were then evaluated for disease severity, utilizing the rating system reported in preceding examples.

In each test, there were a plurality of three replicates and two controls: (1) water containing 0.5 percent ethanol and 0.1 percent of polyoxyethylene sorbitan monolaurate; and (2) plain water.

The results of these evaluations were as set forth in the following tables.

TABLE 8
SEED-SOAK EVALUATIONS

| Compound | Conc. of Compounds in Treating Solution* | Grams of Compound/ 100 lbs. Seed | Disease Rating |
|---|---|---|---|
| 3-Methyl-s-triazolo(3,4-b)-benzothiazole | 1000 | 45.4 | 4 |
|  | 500 | 22.7 | 3 |
|  | 250 | 11.4 | 2 |
| 3-Chloro-s-triazolo(3,4-b)-benzothiazole | 1000 | 45.4 | 5 |
|  | 500 | 22.7 | 4+ |
|  | 250 | 11.4 | 3 |
| 5-Chloro-s-triazolo(3,4-b)-benzothiazole | 1000 | 45.4 | 5 |
|  | 500 | 22.7 | 5 |
|  | 250 | 11.4 | 4+ |
|  | 175 | 7.8 | 3+ |
|  | 100 | 4.5 | 3 |
| 5-Methyl-s-triazolo(3,4-b)-benzothiazole | 1000 | 45.4 | 5 |
|  | 500 | 22.7 | 4+ |
|  | 250 | 11.4 | 4 |
|  | 175 | 7.8 | 3− |

*In ppm. (based on seed weight)

While the triazolobenzoxazole and triazolobenzothiazole compounds are useful in accordance with the present invention when employed individually or in combination with one another, the present invention also encompasses the use of these compounds in combination with other known fungicides, herbicides, or other plant treating substances.

The following examples illustrate such combined therapy.

EXAMPLES 168-177

5-Chloro-s-triazolo(3,4-b)benzothiazole was evaluated in combination with numerous other substances for the control of rice blast, helminthosporium, and late blight on young plants of rice (variety, Nato), Penrod barley, and tomato (variety, Bonny Best), respectively. Each compound or combination of compounds was applied to the foliage by spraying in a conventional formulation. When the foliage had dried, the plants were inoculated with *Piricularia oryzae, Helminthosporium sativum,* and *Phytophthora infestans,* respectively; and the inoculated plants were incubated for 48 hours at 18° C. in a moist chamber. The plants were then held under typical greenhouse conditions. The plants were observed for development of disease at about 5 days after spraying. The results (an average of two replicates for each treatment) were as set forth in the following table.

Table 9

| | Dosages (ppm. active) | Average Disease Ratings | | |
|---|---|---|---|---|
| | | Rice Blast | Helminth. | Late Blight |
| A | 25 | 4+ | 2+ | 1 |
| | 5 | 3+ | 2+ | 2+ |
| A+B | 25 + 600 | 4+ | 3 | 2− |
| | 5 + 200 | 4− | 3− | 1+ |
| B | 600 | 1 | 2+ | 1+ |
| | 200 | 1+ | 2 | 2+ |
| A+C | 25 + 400 | 4+ | 3− | 3+ |
| | 5 + 100 | 3+ | 2+ | 3+ |
| C | 400 | 2+ | 4− | 4+ |
| | 100 | 1+ | 3− | 4 |
| A+D | 25 + 400 | 5 | 4+ | 4+ |
| | 5 + 100 | 4 | 4− | 4 |
| D | 400 | 3− | 4 | 4+ |
| | 100 | 2 | 3 | 4+ |
| A+E | 25 + 400 | 5 | 4+ | 4− |
| | 5 + 100 | 4 | 3− | 4− |
| E | 400 | 3 | 4+ | 3− |
| | 100 | 3− | 4− | 3 |
| A+F | 25 + 400 | 4+ | 4+ | 3+ |
| | 5 + 100 | 4− | 3+ | 4+ |
| F | 400 | 2 | 4+ | 3+ |
| | 100 | 2+ | 4+ | 4+ |
| A+G | 25 + 400 | 4+ | 3− | 3+ |
| | 5 + 100 | 4− | 3− | 3 |
| G | 400 | 2 | 3 | 4+ |
| | 100 | 1 | 1+ | 2+ |
| A+H | 25 + 50 | 5 | 2− | 1 |
| | 5 + 10 | 3 | 3 | 1+ |
| H | 50 | 1+ | 3− | 1+ |
| | 10 | 1 | 2+ | 2− |
| A+I | 25 + 25 | 5 | 2+ | 1 |
| | 5 + 5 | 4+ | 2− | 2− |
| I | 25 | 3− | 1 | 2+ |
| | 5 | 1+ | 2− | 1+ |
| A+J | 25 + 25 | 4+ | 1+ | 2+ |
| | 5 + 5 | 4− | 2− | 3 |
| J | 25 | 2 | 1 | 3− |
| | 5 | 1 | 1 | 2 |
| A+K | 25 + 200 | 4+ | 4+ | 2− |
| | 5 + 50 | 4+ | 3− | 1 |
| K | 200 | 1 | 3− | 2− |
| | 50 | 2+ | 2 | 2+ |
| Control | 0 | 1 | 2 | 2 |
| | 0 | 1 | 1 | 1 |

Table 9-continued

| Dosages (ppm. active) | Average Disease Ratings | | |
|---|---|---|---|
| | Rice Blast | Helminth. | Late Blight |
| 0 | 1 | 1 | 1 |

A = 5-Chloro-s-triazolo(3,4-b)benzothiazole
B = Tribasic copper sulfate
C = Mixture of ammoniates of ethylenebis(dithiocarbamate)zinc and ethylenebis(dithiocarbamic acid)bimolecular and trimolecular cyclic anhydrosulfides and disulfides
D = 2,4,5,6-Tetrachloroisophthalonitrile
E = 2,4-Dichloro-6-(o-chloroanilino)-s-triazine
F = Manganous ethylenebisdithiocarbamate
G = N-Trichloromethylthio-4-cyclohexene-1,2-dicarboximide
H = O-ethyl-S,S-diphenyldithiophosphate
I = Pentachloromandelonitrile
J = 1-(Butylcarbamoyl)-2-benzimidazole carbamic acid, methyl ester
K = α-(2,4-Dichlorophenyl)-α-phenyl-5-pyrimidinemethanol

EXAMPLES 178-179

5-Chloro-s-triazolo(3,4-b)benzothiazole was also evaluated for the control of rice blast when the compound was applied in combination with known fungicides and application was made to the water surface. Rice plants were grown in pots flooded with water. The compound or compounds were formulated in conventional procedures and applied to the water surface when the plants were 10 days old. Two replicates were conducted for each compound or combination of compounds. Three days later all plants were inoculated with *Piricularia oryzae* and incubated 48 hours in a moist chamber at 18° C. Thereafter the plants were held under typical greenhouse conditions for 5 days, at which time the plants were evaluated for disease control. The results were as set forth in the following table.

Table 10

| | Dosage (in lbs./acre) | Rice Blast Ratings |
|---|---|---|
| A | 1 | 3+ |
| | 3 | 4+ |
| A+B | 1 + 5 | 4+ |
| | 3 + 10 | 5 |
| B | 5 | 3− |
| | 10 | 3 |
| A+C | 1 + 5 | 4+ |
| | 3 + 10 | 4+ |
| C | 5 | 2+ |
| | 10 | 2 |
| (Solvent Check) | 0 | 1 |

A = 5-chloro-s-triazolo(3,4-b)benzothiazole
B = methyl 1-(butylcarbamoyl)-2-benzimidazolecarbamate
C = 0,0-diisopropyl S-benzyl phosphorothiolate

EXAMPLES 180-182

5-Chloro-s-triazolo(3,4-b)benzothiazole was also evaluated in combination with other substances for the control of rice blast via seed coat treatment.

Rice seed was treated, initially with 5-chloro-s-triazolo(3,4-b)benzothiazole, then with a second substance. These seeds were planted in pots of sterile and non-sterile soil. When the resulting rice seedlings were 3 to 4 inches tall, they were inoculated with *Piricularia oryzae* and incubated as in the preceding example. The plants were then held for 5 days under typical greenhouse conditions, at which time evaluations of disease control were made. The results were as reported in the following table.

Table 11

| | Active Ingredient (ml or g/100kg seed) | Plant Emergence and Rice Blast Ratings 5-Chloro-s-triazolo(3,4-b)benzothiazole | | | | | | | | | | | |
|---|---|---|---|---|---|---|---|---|---|---|---|---|---|
| | | Sterile Soil | | | | | | Non-Sterile Soil | | | | | |
| | | 0 | | 10g/100kg | | 30g/100kg | | 0 | | 10g/100kg | | 30g/100kg | |
| | | E* | RB | E | RB | E | RB | E | RB | E | RB | E | RB |
| Methyl mercury dicyandiamide | 0 | 10 | 1+ | 10 | 5 | 9 | 5 | 1.67 | 1 | 6.67 | 4+ | 4 | 5 |
| | 1.57 ml | 10 | 1+ | 10 | 4+ | 8 | 5 | 9 | 1 | 10 | 4+ | 9 | 5 |
| | 3.15 ml | 10 | 1 | 9 | 4+ | 8 | 5 | 9.33 | 1 | 10 | 5 | 8.67 | 5 |
| Bis(dimethyl-dithiocarbamoyl)-disulfide | 0 | 10 | 2− | 10 | 5 | 9 | 5 | 6.33 | 1 | 1.33 | 4+ | 8.33 | 4+ |
| | 124.6 g | 10 | 1+ | 9 | 5 | 9 | 4+ | 10 | 1 | 9.67 | 5 | 8 | 5 |
| | 249.7 g | 10 | 1 | 9 | 5 | 8 | 5 | 10 | 1 | 9.67 | 5 | 8.33 | 5 |
| N-Trichloromethyl-thio-4-cyclohexene-1,2-dicarboximide | 0 | 10 | 1 | 10 | 4+ | 9 | 5 | 4 | 1 | 5.67 | 4+ | 9 | 5 |
| | 124.6 g | 10 | 1 | 10 | 5 | 9 | 5 | 10 | 1 | 10 | 5 | 8.33 | 5 |
| | 249.7 g | 10 | 1 | 10 | 5 | 9 | 5 | 10 | 1 | 10 | 4+ | 9.67 | 5 |

*E = Plant emergence rating on 0–10 scale, where 10 = 100% of seed germinated and plants emerged above soil.

EXAMPLES 183–184

Each of 5-chloro-s-triazolo(3,4-b)benzothiazole and 3-methyl-s-triazolo(3,4-b)benzothiazole was evaluated for the control of rice blast when applied as a transplant root soak.

Each of the compounds was formulated in a plurality of aqueous suspensions containing varying concentrations of the subject compound but uniformly containing 0.05 percent of a polyoxyethylene sorbitan monolaurate and 1.0 percent of ethanol. The roots of 21-day-old rice plants were immersed for 5 minutes in the suspensions, 36 plants per suspension. The rice plants were then transplanted into containers of flooded soil. After the plants were well established, they were inoculated with *Piricularia oryzae;* the procedures were the same as described in preceding examples. Eleven days later, the plants were observed for rice blast and for crop injury. There were three replications per treatment rate. In addition to the rice plants treated with either of the subject compounds, a group of rice plants was root-soaked for 5 minutes in an aqueous solution containing 1.0 percent of ethanol and 0.05 percent of the same polyoxyethylene sorbitan monolaurate, and another group was root-soaked for 5 minutes with water alone, both to serve as controls.

The results were as set forth in the following table. Rice blast ratings were made by the same scale as previously used; crop injury was rated on a scale of 0–10 with 0 = all plants healthy and 10 = all plants dead.

TABLE 12

RICE BLAST AND CROP INJURY RATINGS, TRANSPLANT ROOT SOAK APPLICATION

| Compound | Percent Concentration of Compound in Soak Solution | Rice Blast Ratings | Crop Injury |
|---|---|---|---|
| 5-Chloro-s-triazolo-(3,4-b)benzothiazole | 0.05 | 3+ | 0 |
| | 0.1 | 4+ | 0.3 |
| | 0.2 | 4+ | 0 |
| 3-Methyl-s-triazolo-(3,4-b)benzothiazole | 0.05 | 3− | 0 |
| | 0.1 | 4− | 0.3 |
| | 0.2 | 3− | 1.3 |
| Aqueous Solution containing 1.0% ethanol and 0.05% polyoxyethylene soritan monolaurate | — | 1 | 0.6 |
| Water | — | 1 | 0 |

EXAMPLES 185–186

Each of 5-chloro-s-triazolo(3,4-b)benzothiazole and 3-methyl-s-triazolo(3,4-b)benzothiazole was evaluated for the control of leaf rust (*Puccinia recondita*) on wheat by seed coat application.

Quantities of wheat seed of the Monon variety were coated with liquid formulations containing the subject compounds. More particularly, two precurser formulations of each compound were utilized, a 15 percent wettable powder ("15W") and a 25 percent wettable powder ("25W"). Each was mixed with several small portions of water, about 3 percent by weight of the seed to be treated with the respective formulation. Thus, from each precursor formulation, a plurality of treating formulations was obtained varying in the amount of compound applied to the seeds treated with the respective formulation (expressed as grams of compound per 100 kilograms of seed). After treatment, the seeds were planted. Other seed, left untreated to serve as a control, was also planted. All plantings were held under normal agricultural conditions until the emerging wheat seedlings were 3 inches high. All plants were then inoculated with spores of leaf rust (*Puccinia recondita*) and incubated for 48 hours in a moist chamber at 65° F. The plants were again held under normal growing conditions for 8 days, at which time the plants were observed for crop injury and leaf rust incidence.

The results were as set forth in the following table. Leaf rust was rated on a scale of 1–5 with 1 = heavy incidence of disease and 5 = no disease symptoms. Crop injury was not numerically rated but was noted as to type, when present.

TABLE 13

LEAF RUST AND CROP INJURY RATINGS, SEED COAT APPLICATION

| Compound | Formulation | Grams of compound/100 kilograms of seed | | | |
|---|---|---|---|---|---|
| | | 100 | 200 | 400 | 600 |
| 3-Methyl-s-triazolo-(3,4-b)benzothiazole | 15W | thin 2 stand | 3 | 4− | N.T.* |
| | 25W | 3− | 4 | 5 | 5 slight stunting |
| 5-Chloro-s-triazolo-(3,4-b)benzothiazole | 15W | thin 3 stand | stunt-3 ing | some 2 stunting | N.T.* |
| | 25W | 2− | 3—stunting | No plants | No plants |
| (Control) | | 1+ | | | |

*N.T. = not tested

EXAMPLES 187–188

Each of 3-methyl-s-triazolo(3,4-b)benzothiazole and 3-chloro-s-triazolo(3,4-b)benzothiazole was evaluated for control of leaf spot on wheat (*Helminthosporium*

*sativum*). Application of the compounds was by the seed coat technique. The evaluation procedures were the same as set forth in Examples 185-186 except that the inoculation was with *Helminthosporium sativum*. The results were as set forth in the following table.

TABLE 14
LEAF SPOT AND CROP INJURY RATINGS, SEED COAT APPLICATION

| Compound | Form-ulation | Grams of compound/100 kilograms of seed | | | |
|---|---|---|---|---|---|
| | | 100 | 200 | 400 | 600 |
| 3-Methyl-s-triazolo-(3,4-b)benzothiazole | 15W | 3+ | 3+ | 3+ | N.T.* |
| | 25W | 3 | 3 | 3+ | 3+ |
| 3-Chloro-s-triazolo-(3,4-b)benzothiazole | 15W | 2— | 3+ | 4+ | N.T.* |
| | | | | stunt- | stunt- |
| | 25W | 1 | 4— | 2 ing | 4 ing |
| (Control) | — | 1 | | | |

*N.T. = not tested

EXAMPLES 189-190

Each of 5-chloro-s-triazolo(3,4-b)benzothiazole and 5-methyl-s-triazolo(3,4-b)benzothiazole was evaluated for the control of rice blast (*Piricularia oryzae*) when applied to boxes of young rice plants shortly prior to transplanting. More particularly, 270 grams of soaked rice seed were seeded to clay loam in each nursery box, 28 × 58.5 × 3 cm., permitted to germinate, and reared to the stage of 4-5 leaves with 15-18 cm. leaf length. At this stage, each box of plants to be treated was immersed for 15 minutes in a treating solution containing the respective compound. The compounds were present in the solutions in various concentrations. The uptake of treating solution averaged 1.2 liters per nursery box. The plants so treated, as well as control plants left untreated, were transplanted into rice paddies on the same day. Approximately two months later, the rice plants were observed for rice blast control, plant height, and the number of tillers per plant. The results were as set forth in the following table:

| Treatment | Rate (ppm) | Percent Leaf Blast Control a/ | Plant Height (cm) b/ | No. of Tillers/ Plant b/ |
|---|---|---|---|---|
| 5-Chloro-s-triazolo(3,4-b)benzothiazole | 1000 | 0 | 64 | 15.6 |
| | 4000 | 22 | 66 | 14.2 |
| 5-Methyl-s-triazolo(3,4-b)benzothiazole | 1000 | 15 | 65 | 15.0 |
| | 4000 | 51 | 67 | 13.7 |
| Control | 0 | 0 | 65 | 14.5 |
| | | (24) c/ | | | a/ The percent rice blast (*Piricularia oryzae* on rice leaves leaves was determined by evaluating the degree of infection and type of lesion on 100 plants per plot.
b/ The average plant height and number of tillers per plant was determined by evaluating 100 plants per plot.
c/ Percent infection on the leaves of untreated plants.

EXAMPLES 190-191

5-Methyl-s-triazolo(3,4-b)benzothiazole was evaluated further for the control of rice blast (*Piricularia oryzae*). Treatment was by two different methods, the one being the immersion of nursery boxes of rice seedlings, in the same manner as described in the preceding examples. The second method of application was a soil drench of nursery boxes containing rice seedlings, the boxes being the same size as described in the preceding example. Each such box was drenched with 0.5 liter of treating solution, the concentration of the compound being adjusted to provide specified application rates in kilogram per hectare basis. The plants were transplanted to rice paddies. Observations were made 2 months later; the results were as follows.

| Treatment | Rate | Percent Leaf Blast Control a/ | Plant Height (cm) b/ | No. of Tillers Plant b/ |
|---|---|---|---|---|
| Flat drench; transplanting thirteen to fourteen hours later | (kg/ha) | | | |
| | 5 | 25 | 77 | 15.5 |
| | 10 | 31 | 75 | 14.6 |
| | 20 | 21 | 79 | 15.9 |
| | 40 | 68 | 79 | 16.2 |
| | 80 | 56 | 78 | 15.6 |
| 15 minute root soak; transplanting same day. | (ppm) | | | |
| | 500 | 19 | 78 | 16.4 |
| | 1000 | 43 | 77 | 13.6 |
| | 2000 | 27 | 77 | 13.7 |
| | 4000 | 57 | 78 | 15.8 |
| | 8000 | 71 | 75 | 14.7 |
| Control | 0 | 0 | 78 | 16.4 |
| | | (16) c/ | | | a/ The percent rice blast (*Piricularia oryzae*) on rice leaves was determined by evaluating the degree of infection and type of lesion on 100 plants per plot.
b/ Plant average height and number of tillers per plant was determined by evaluating 100 plants per plot.
c/ Percent infection on the leaves of untreated plants.

The 2-(2-acylhydrazino)benzoxazole and 2-(2-acylhydrazino)benzothiazole compounds to be employed as starting materials:

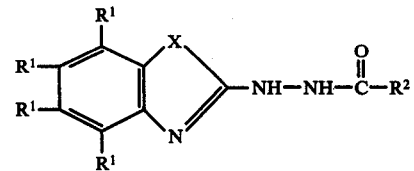

are themselves prepared in conventional procedures for the preparation of hydrazides. Conveniently, the corresponding 2-hydrazino compound

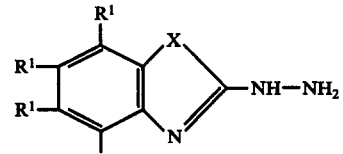

is reacted with an acyl halide

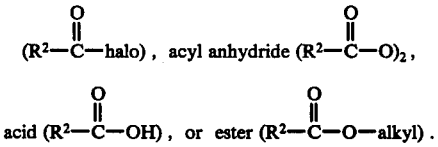

The reaction is conducted in accordance with conventional procedures. The 2-hydrazinobenzoxazole and 2-hydrazinobenzothiazole compounds are readily prepared in known procedures. In one procedure, the corresponding 2-amino compound is diazotized and displaced by chloride, which is then displaced with hydrazine. In another, the mercapto group of the corresponding 2-mercapto compound is displaced with hydrazine: cf. *J. Chem. Soc.*, 1949, 355. In yet another procedure, an exchange amination, the amino group of the corresponding 2-amino compound is replaced by hydrazino: cf. *J. Gen. Chem.* U.S.S.R. (Eng. translation), Vol. 29, pg. 2036 (1959). In an improvement of the last of these procedures, the reaction is catalyzed by acid, and the reactants are employed in amounts representing a ratio of one molecular proportion of 2-amino compound to from one to five molecular proportions of hydrazine, preferably about three.

In the instance of 3-methyl-s-triazolo(3,4-b)benzothiazole, one of the compounds to be employed in accordance with the present invention, it has been noted that a hydrate readily forms under conditions normally used for formulating agriculatural chemicals. More particularly, when the compound has been added to water, initially there has been formed a viscous fluid. Addition of further amounts of water converted the viscous fluid into a solution. Drying of the viscous fluid resulted in a powder which analyzed correctly for the monohydrate. This monohydrate in any form can be used as the active agent in accordance with the present invention; seed treatment. Other compounds to be employed in accordance with the present invention may also form hydrated substances useful in the practice of the present invention.

I claim:

1. A method for protecting a plant against attack by a plant-pathogenic bacterial or fungal organism which comprises applying to a locus of the organism an effective amount of an active agent selected from the group consisting of the compounds of the formula

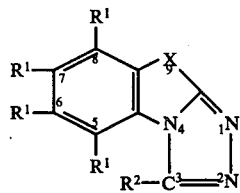

and the phytologically acceptable acid addition salts thereof, wherein

X represents —O—, —S—,

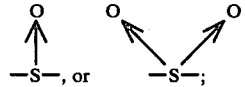

each $R^1$ independently represents hydrogen, halo, lower alkyl of $C_1$-$C_3$, lower alkoxy of $C_1$-$C_3$, or lower alkylthio of $C_1$-$C_3$;

$R^2$ represents hydrogen, alkyl of $C_1$-$C_{11}$, cyclopropyl, hydroxy, lower alkoxy of $C_1$-$C_3$, mercapto, lower alkylthio of $C_1$-$C_3$, allylthio, propynylthio, benzylthio, halo, amino, (lower alkyl of $C_1$-$C_3$)amino, di(lower alkyl of $C_1$-$C_3$)amino, carbamoyl, thiocyanato, acetamido, trifluoromethyl, halomethyl, mono- or di(lower alkyl of $C_1$-$C_3$)aminomethyl, or radical of the formula

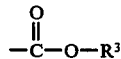

wherein $R^3$ represents sodium, potassium, or lower alkyl of $C_1$-$C_3$;

subject to the limitations (1) that at least two $R^1$'s, or at least one $R^1$ and $R^2$, represent hydrogen, and (2) that when both $R^2$ and the $R^1$ substituent at the 5-position represent groups other than hydrogen, such groups together do not contain more than six carbon atoms.

2. The method of claim 1 wherein the plant pathogen is a fungus.

3. The method of claim 2 wherein the fungus is the causal agent of rice blast (*Piricularia oryzae*).

4. The method of claim 3 wherein the active agent is 5-methyl-s-triazolo(3,4-b)benzothiazole.

5. The method of claim 2 wherein the active agent is 3-methyl-s-triazolo(3,4-b)benzothiazole.

6. The method of claim 2 wherein the active agent is 3-methyl-s-triazolo(3,4-b)benzoxazole.

7. The method of claim 2 wherein the active agent is 3-chloro-s-triazolo(3,4-b)benzothiazole.

8. The method of claim 2 wherein the active agent is 5-chloro-s-triazolo(3,4-b)benzothiazole.

9. The method of claim 2 wherein the active agent is 5-methyl-s-triazolo(3,4-b)benzothiazole.

10. A composition suitable for protecting a plant against attack by a plant pathogenic bacterial or fungal organism which comprises a surface active dispersing agent, an inert finely divided solid, and an effective amount from about 2 to 98 percent by weight of an active agent selected from the group consisting of compounds of the formula

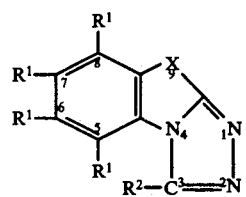

and the phytologically acceptable acid addition salts thereof, wherein

X represents —O—, —S—,

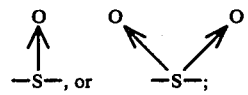

each $R^1$ independently represents hydrogen, halo, lower alkyl of $C_1$-$C_3$, lower alkoxy of $C_1$-$C_3$, or lower alkylthio of $C_1$-$C_3$;

$R^2$ represents hydrogen, alkyl of $C_1$-$C_{11}$, cyclopropyl, hydroxy, lower alkoxy of $C_1$-$C_3$, mercapto, lower alkylthio of $C_1$-$C_3$, allylthio, propynylthio, benzylthio, halo, amino, (lower alkyl of $C_1$-$C_3$)amino, di(lower alkyl of $C_1$-$C_3$)amino, carbamoyl, thiocyanato, acetamido, trifluoromethyl, halomethyl, mono- or di(lower alkyl of $C_1$-$C_3$)aminomethyl, or radical of the formula

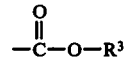

wherein $R^3$ represents sodium, potassium, or lower alkyl of $C_1$-$C_3$;

subject to the limitations (1) that at least two $R^1$'s or at least one $R^1$ and $R^2$, represent hydrogen; and (2) that when both $R^2$ and the $R^1$ substituent at the 5-position represent groups other than hydrogen, such groups together do not contain more than six carbon atoms.

11. The composition of claim 10 wherein the active agent is 3-methyl-s-triazolo(3,4-b)benzothiazole.

12. The composition of claim 10 wherein the active agent is 3-methyl-s-triazolo(3,4-b)benzoxazole.

13. The composition of claim 10 wherein the active agent is 3-chloro-s-triazolo(3,4-b)benzothiazole.

14. The composition of claim 10 wherein the active agent is 5-chloro-s-triazolo(3,4-b)benzothiazole.

15. The composition of claim 10 wherein the active agent is 5-methyl-s-triazolo(3,4-b)benzothiazole.

16. 5-Chloro-s-triazolo(3,4-b)benzothiazole.

17. 5-Fluoro-s-triazolo(3,4-b)benzothiazole.

18. 5-Methyl-s-triazolo(3,4-b)benzothiazole.

* * * * *